United States Patent
Carns

Patent Number: 5,195,997
Date of Patent: Mar. 23, 1993

[54] INCONTINENT'S AID

[76] Inventor: William A. Carns, 629 E. 10th Ave., Ste. 4, Apache Junction, Ariz. 85219

[21] Appl. No.: 799,088

[22] Filed: Nov. 27, 1991

[51] Int. Cl.$^5$ ............................................. A61F 5/44
[52] U.S. Cl. ............................ 604/347; 128/761;
604/349; 604/352; 604/353
[58] Field of Search ............ 604/347, 349–350;
128/760, 761; 4/144.1, 144.3, 144.4; 137/605

[56] References Cited

U.S. PATENT DOCUMENTS

| | | | |
|---|---|---|---|
| 2,594,476 | 4/1952 | Miller | 137/605 |
| 2,645,277 | 7/1953 | Richter | 137/605 |
| 2,785,014 | 3/1957 | Pro | 137/605 |
| 2,889,995 | 6/1959 | Borell | 137/605 |
| 3,349,768 | 10/1967 | Keane | 604/347 |

*Primary Examiner*—Randall L. Green
*Assistant Examiner*—R. Clarke
*Attorney, Agent, or Firm*—James F. Duffy

[57] ABSTRACT

A urine collection vessel is coupled to the body of a person by means of a partial vacuum created within the collection vessel. An air flow valve at the output of the vessel is adjustable to control the degree of a partial vacuum created within the vessel as well as establishing control over the velocity of air flow through the valve and down the associated conduit through which urine is conducted to a reservoir in which the urine is accumulated. The device is intended for use primarily by people who are troubled with prostate or bladder problems which, without the use of the invention, would make it necessary for these persons to frequently fully rouse themselves from sleep and to exit from their beds in order to void their bladders in the course of the night.

13 Claims, 2 Drawing Sheets ial Field of the Invention

INCONTINENT'S AID

BACKGROUND

1. Technical Field of the Invention

The invention relates to the field of apparatus which provides relief to persons who are incontinent or who, due to prostate or bladder problems, must make frequent trips to the bathroom to urinate. The invention is particularly dedicated to apparatus which a person may utilize to assure a relatively uninterrupted night's sleep without the necessity to leave their bed in order to urinate.

2. Prior Background Art

Much of the prior art is dedicated to devices for drawing off urine and collecting it in a reservoir. U.S. Pat. No. 3,421,504, to Gibbons issued Jan. 14, 1969 is a device of last resort, to be used in unblocking the male urinary tract. A condom-like sheath is affixed to the male penis and a manually operated vacuum pump is exercised for purposes of clearing the male urinary tract. Because a significantly high vacuum level is required heavy walled tubing is necessary to prevent the tubing from collapsing. This is not a device to be used to assist an incontinent patient or to permit a patient with bladder or prostate problems to have an uninterrupted night's sleep.

The apparatus of Terauchi, disclosed in U.S. Pat. No. 4,281,655 issued Aug. 4, 1981 provides a collector for use with the male patient. The collector is such that urine may accumulate unless the penis extends well into the receptacle. The possibility therefore exists of urine accumulation within the collector, which accumulation may cause irritation of the patient's skin. In addition, the construction is such that the head of the male penis could become entrapped within the outlet of the collection device since the device is connected to a vacuum pump. The collection device is retained on the body of the male by means of straps. No utilization of the vacuum is employed to aid in retention of the device on the male body.

Izumi discloses a vacuum suction type urinating aid in U.S. Pat. No. 4,531,939, issued Jul. 30, 1985. However, it suffers from two inadequacies overcome by the present invention. The Izumi device does not utilize suction as an aid in holding the device in place on the body. Further, the head of the penis can be drawn into the urine outlet and held there by suction. The Izumi device is a manually operated device and the patient must be fully awake to utilize it. It does not offer the patient the opportunity of a full and uninterrupted night's sleep.

Breer sets out a body liquid collector appliance in U.S. Pat. No. 3,112,061, issued Nov. 26, 1963. Breer discloses a crotch conforming sack held in place by both suction and belts. He recognizes the advantage of suction is drawing off urine. But he provides no bleeder valve, as does the inventor herein, to encourage the flow of urine through the transfer tube or to adjust the degree of retention of the device on the patient's body. Breer has a continuously operating vacuum pump which, because there is no air bleeder provided in his system, could result in collapse of the crotch conforming collector vessel as well as the transfer conduit.

In U.S. Pat. No. 4,084,589, issued Apr. 18, 1978 to Kulvi, there is disclosed a urine collection bag affixed to the body by means of adhesive tape and having a continuous air flow therethrough to assist the transfer of urine from the collection bag into a reservoir. There is no vacuum assistance to retain the collection device on the body of the patient and there are no control means for controlling the flow of air and the velocity of transfer of the fluid.

It is an object of the invention to provide apparatus which may be utilized by both the incontinent person as well as by the person who must make frequent repeated visits to the bathroom to void their urine. Among the latter persons are males with prostate problems as well as male and female patients having bladder problems.

Most persons who are incontinent are unaware of the fact that they are voiding their bladder until that act has been achieved or essentially accomplished. Such persons resort to special underwear often equated to the diapers that a young child may wear.

For persons having prostate or bladder problems the need to urinate is consciously communicated to that person. Thus, in the course of an evening their sleep is interrupted and they must leave their bed in order to urinate. They experience an urgent need to urinate, which need arises every 15 or 20 minutes, if not more frequently. The person's ability to obtain a healthful night's rest is thus obviated; and the lack of sleep, coupled with the demoralizing aspects of their problem, reduces the person to an even sorrier state of health.

It is the intent of the invention to enable a person suffering from incontinence to avoid the necessity of wearing diaper-like underclothing and to assist those persons suffering from prostate or bladder problems to have a restful and uninterrupted night's sleep.

SUMMARY DESCRIPTION OF THE INVENTION

The invention is an improvement in prior art apparatus for receiving, transferring and accumulating fluids excreted from the body. Such prior art apparatus has fluid collection means which is coupled to the body for receiving those fluids, reservoir means for accumulating the fluids, and hollow conduit means for transferring the fluids from the collection means to the reservoir means. The prior art apparatus includes air flow impelling means for drawing air into the collector through the conduit means and the reservoir so as to enhance the flow of the fluid from the collector to the reservoir. The improvement set forth herein comprises air flow control means coupled to the collection means for reducing the air flow through the conduit. This reduction of air flow achieves two affects. It creates a partial vacuum within the collection means whereby the collection means is retained in place on the patient's body. Second, its affect is that of increasing the velocity of air flowing through the conduit such that the flow of excreted body fluids from the collection means to the reservoir through the conduit is aided and enhanced.

Disclosed herein, as part of the improvement of the prior art devices is a means for varying the degree of reduction of the air flow through the conduit. This variable control means adjusts the degree of the partial vacuum within the collection means as may be dictated by the comfort of the person on whose body the collection means is retained by reason of the partial vacuum. Also, the variable control means permits adjusting the air flow rate of evacuation of fluid from the collection means.

In one presently preferred embodiment of the invention, the collection means is a condom-like sheath which accepts the male penis and is retained on the penis by the partial vacuum created by the air flow control means. The placement of the air flow control means just forward of the tip of the penis precludes the possibility of the head of the penis being drawn into the air flow conduit entrance.

In an alternative embodiment of the invention, the collection means is a fluid collection vessel which conforms to the anatomy of a woman's public region so as to encompass the female urinary outlet areas. This collection vessel is retained coupled to the female body by the partial vacuum created by the air flow control means.

Applicable to all of the embodiments of the invention disclosed is the improvement wherein the air flow means is a continually operating air pump. In a preferred embodiment, the air pump is a vibratory air pump of the type frequently utilized with home type fish aquariums. These vibratory air pumps have been found to output a soothing sound which tends to relax a person and induce sleep.

DETAILS OF BEST MODE FOR CARRYING OUT THE INVENTION

Figure 1:
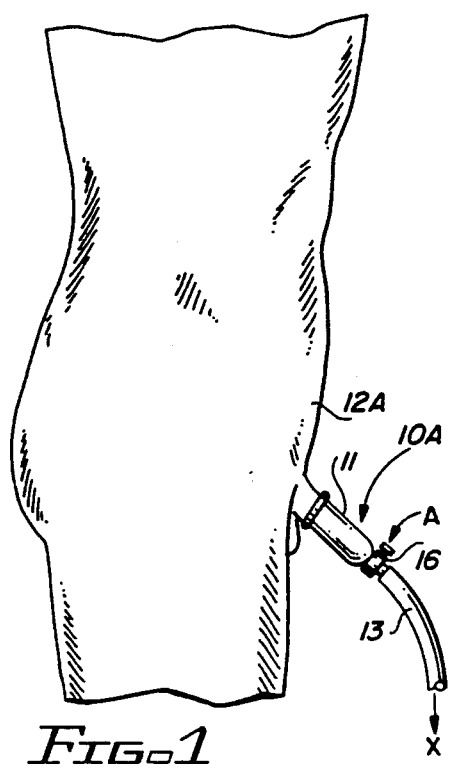
FIG. 1 illustrates a male form with a urine collector encompassing the male's penis. Urine is drawm off by a conduit to a collection point X.

For purposes of promoting an understanding of the principles of the invention, reference will now be made to the embodiments illustrated in the drawings and specific language will be used to describe same. it will nevertheless be understood that no limitation of the scope of the invention is thereby intended, there being contemplated such alterations and modifications of the illustrated device, and such further applications of the principles of the invention as disclosed herein, as would normally occur to one skilled in the art to which the invention pertains.

The devices herein disclosed represent improvements over prior art devices for the collection and accumulation of urine from the human body. As a result of the improvements to be herein disclosed, the invention may readily be utilized by persons within the confines of their home to relieve them of the uncomfortable after-effects of incontinence or to allow those suffering prostate or bladder problems to obtain a restful uninterrupted night's sleep. The apparatus is retained on the body of the person utilizing the devices by means of a partial vacuum created within the urine collection vessels. The degree of vacuum is controllable by the person so that the collection vessel may be comfortable retained on the body of the person utilizing the device. Because of the retention by partial vacuum, males may utilize the device without the necessity of the use of straps, adhesive, or other methods of retaining the collection vessel in place. The same is true of the embodiment utilized by females, however, some women may want the further assurance provided by use of a modified, elasticized panty to provide them with peace of mind that the apparatus will not be displaced during nocturnal movements in the course of their sleep.

Figure 2:
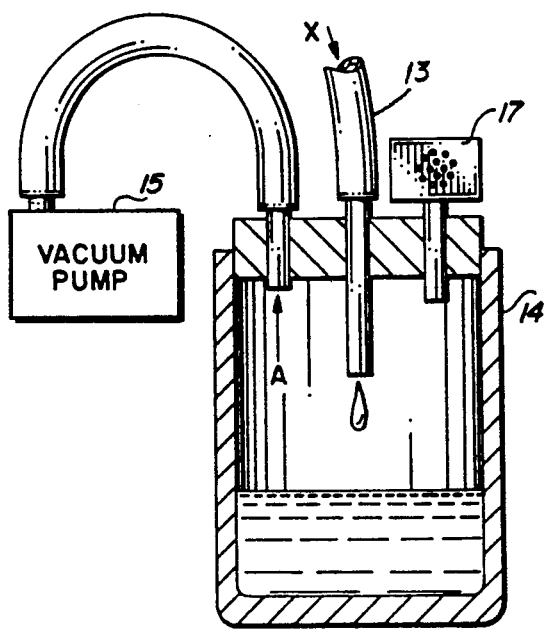
FIG. 2 is an illustration of a reservoir having as its input collection point X for the collection of urine.

The urine recovery device is designed to be worn on a person 12 and to be retained in place by means of partial vacuum created within the urine collection vessel. In FIG. 1 a male person 12A is seen wearing the male embodiment of the invention 10A. In this embodiment the collection vessel 11 is comprised of a condom-like sheath 11 into which the male penis is inserted. Sheath 11, like a condom, closely encompasses the penis. At the tip of the sheath a hollow conduit 13 is attached to transfer urine to a collection reservoir 14, illustrated in FIG. 2. Between sheath 11 and conduit 13 is interposed a variable air flow valve 16. Air flow, indicated by the arrow A enters air valve 16 and travels down conduit 13. The amount of air entering conduit 13, as well as the velocity of air passing down conduit 13 is controlled by valve 16. Conduit 13 of FIG. 1 continues to point X of FIG. 2. Urine excreted by person 12A travels the length of conduit 13 and enters reservoir 14 wherein it is accumulated. Air traveling down conduit 13 is drawn into reservoir 14 by vacuum pump 15. The air flow out of reservoir 14 to vacuum pump 15 is indicated by the arrow A within reservoir 14.

While the invention may be used with patients who are unconscious of their surroundings, it is primarily intended for use with persons who are conscious of their own needs and condition. Thus, a male placing sheath 11 on his penis will adjust air flow control valve 16 so as to reduce the air flow therethrough thereby creating, with the assistance of vacuum pump 15, a partial vacuum within sheath 11. The person may adjust the degree of this partial vacuum so that sheath 11 is established comfortably on the penis without excessive compression thereof. As the air flow orifice of valve 16 is reduced to provide the partial vacuum necessary to maintain sheath 11 in position, the air flow exits valve 16 at a higher velocity. This higher velocity air flow enhances the transfer of urine through conduit 13 into reservoir 14.

It should be noted that placement of valve 16 just forward of the location of the patient's penis in sheath 11 precludes the possibility of the head of the penis being drawn into and blocking the conduit 13.

As noted earlier in this Specification, in the Summary of the Invention, the presently preferred embodiment of the invention utilizes a vacuum pump 15 of the type frequently used with home type, fish aquariums. These pumps are know generally as "vibrator pumps" or "vibratory pumps." The names impliedly characterize the operating characteristics of the pump. The operation is well known and old in the art. Such pumps, for example, are available from Willinger Bros., Inc., Oakland, N.J. 07436.

Figure 6:
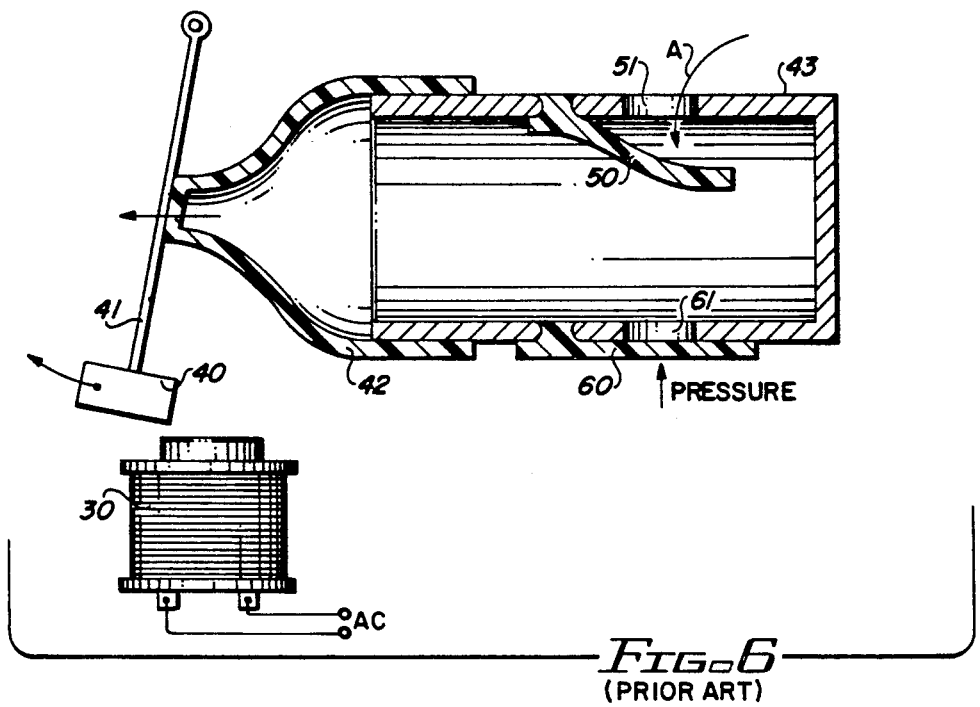
FIG. 6 is a mechanical illustration a first stage of operation of a vibrator pump in which the diaphragm is extended.
Figure 7:
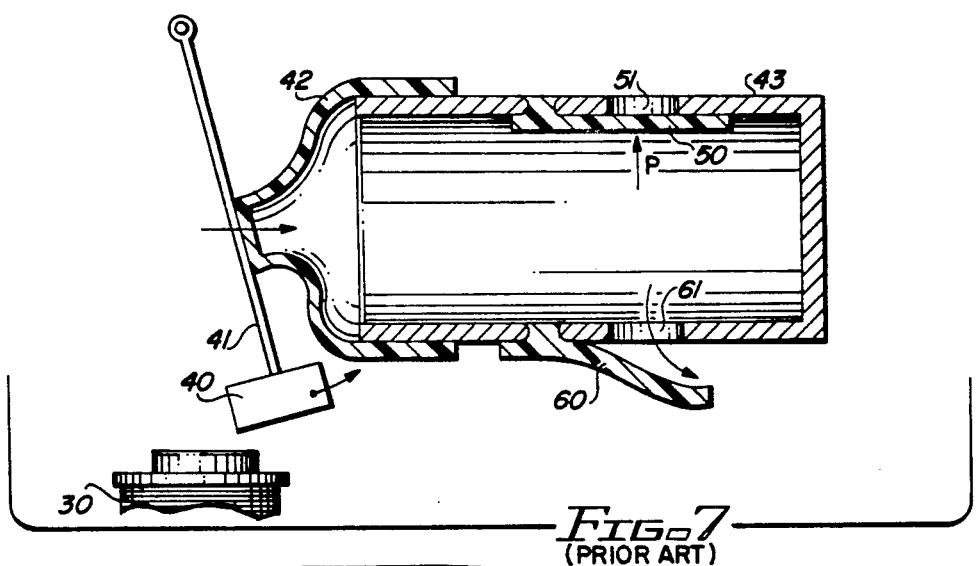
FIG. 7 is a mechanical illustration of a second stage of operation of a vibrator pump in which the diaphragm is compressed.

The basic operation, FIGS. 6 and 7, derives from the interaction between an a.c. energized magnet solenoid 30 and a "pendulum-mounted" permanent magnet 40.

Generally the magnet 40 is supported at the end of a thin, compliant, leaf spring 41. Permanent magnet 40 is alternately attracted and repelled by the solenoid 30. Leaf spring 41 moves back and forth with permanent magnet 40. A flexible diaphragm 42 is coupled to the leaf spring 41 and is distorted by movement of the spring.

This distortion of diaphragm 42 draws air into, or out of, a cylinder 43 capped by diaphragm 42. Flapper valves, 50 and 60, actuated by differential pressures produced by the distortion of diaphragm 42, allow air to enter or leave the cylinder through entry and egress ports, 51 and 61 emplaced in the wall of cylinder 43 and covered by the flapper-type, check valves 50 and 60. Printed illustrations and theory of operation of the vibratory pump are usually provided with the pump at the time of purchase at an aquarium supply store.

In FIG. 6, permanent magnet 40 is being repelled to the left of the illustration, producing an extension of diaphragm 42. When diaphragm 42 is extended, the air pressure in cylinder 43 is reduced causing flapper valve 50 to be drawn downward into cylinder 43 as air flows into the cylinder via suction inlet port 51.

The air pressure external of cylinder 43 forces flapper valve 60 into sealing contact with air outlet 61.

In FIG. 7, magnet 40 is being repelled to the right of the illustration, producing a compression of diaphragm 42. When diaphragm 42 is compressed, the air pressure in cylinder 43 is increased causing flapper value 60 to be drawn downward away from cylinder 43 as air flows out of the cylinder via air outlet 61.

The air pressure internal of cylinder 43 forces flapper valve 50 into sealing contact with suction inlet port 51.

Figure 8:
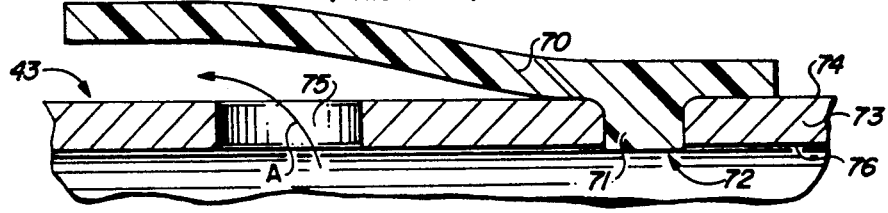
FIGS. 8 and 9 illustrate a conventional method by which a flapper valve is attached to a cylinder wall of a vibrator diagram; and the ease with which pump operation may be modified by reversal of flapper valve placement.
Figure 9:
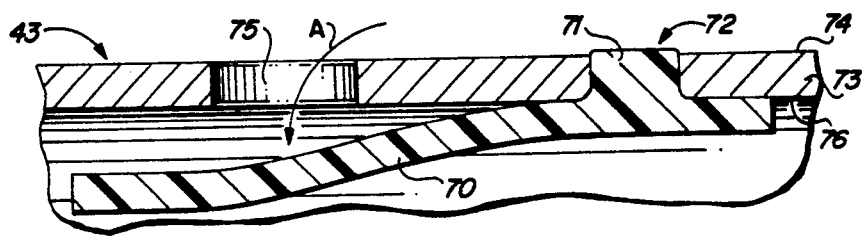

FIGS. 8 and 9 illustrate the manner in which a flapper valve 70 may be installed to convert a valve and port combination from forced air output to suction operation. Typically, flapper valves, such as valve 70, have a projection 71 which is inserted into a through-bore 72 in the wall of the cylinder of a vibrator pump. In FIG. 8, projection 71 is inserted into bore 72 from the top side 74 of wall 73. With this arrangement, air exits from the cylinder when the pump's diaphragm is compressed.

In FIG. 9, projection 71 is inserted into bore 72 from the bottom side 76 of wall 73. With this arrangement, air flows into the cylinder when the pump's diaphragm is extended. The ease with which projection 71 may be removed and reinserted into bore 72 makes it a simple matter to reverse the operation of a vibrator pump from a forced air pump to a suction pump. Thus, if a suction pump is not readily available for practicing the invention, a forced air pump may be procured and easily converted to a suction pump.

Because the solenoid windings are energized by alternating current, a low intensity, but audible, line frequency hum is produced, typically at 60 Hertz. The movement of permanent magnet 40, leaf spring 41, and diaphragm 42, support and reinforce the sound of the hum. Because the invention is used, perforce, in close proximity to the person experiencing incontinence, or the like, that person is exposed to the sound of the hum of the vibratory air pump. Experience has shown that the low intensity hum lulls a person, generally producing relaxation and sleep.

It is intended that vacuum pump 15 shall operate continuously. In this manner, a person may void their urine without having to fully rouse themselves and arise from their bed. No action on the part of the person to activate the system is required. However, with a continuously actuated vacuum pump 15, any blockage of the conduit 13 or valve 16 would tend to defeat the action of the system. To alert the user, should such a situation arise, an audible signaling device 17 is provided. Should air flow cease to flow through conduit 13 into reservoir 14, the pressure within reservoir 14 will be significantly reduced. This reduction in internal pressure within reservoir 14 will cause the air to seek a secondary path through audible alarm 17 to vacuum pump 15. Audible alarm 17 is tripped at a selected differential pressure between the exterior and the interior of reservoir 14 and the subsequent air flow through alarm 17 causes an audible signal which alerts the user of the device that air is not flowing through the conduit 13 as required.

Figure 3:
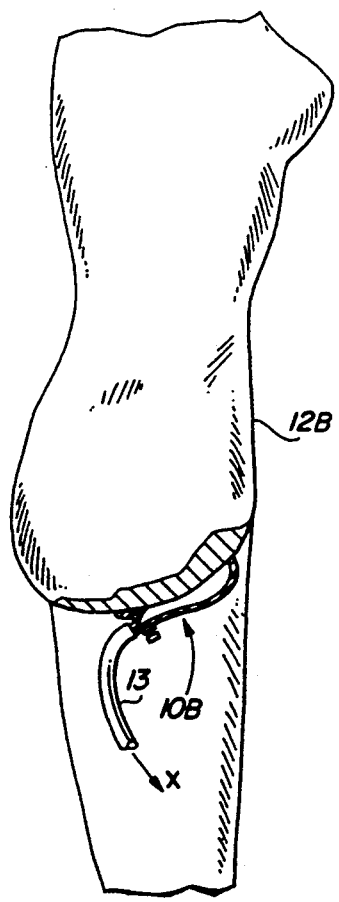
FIG. 3 illustrates an adaptation of the urine collection apparatus for use with female persons.
Figure 4:
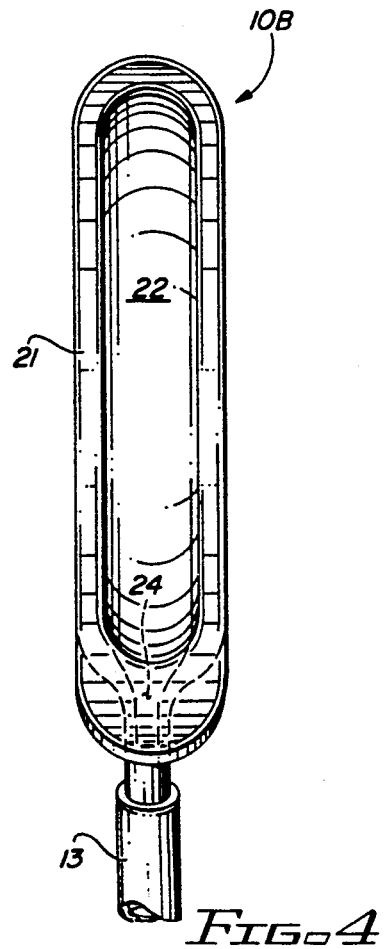
FIG. 4 is a front elevation of the input side of the urine collection apparatus of FIG. 3.
Figure 5:
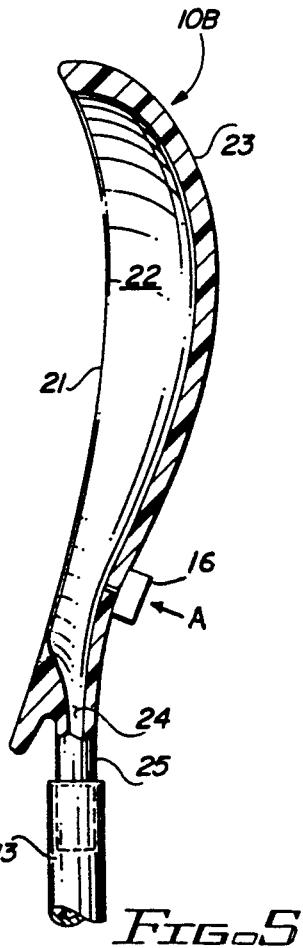
FIG. 5 is a sectional, side elevation of the apparatus of FIG. 4.

The invention may be configured to meet the needs of female anatomy. In FIG. 3 a female person 12B is seen wearing the female embodiment 10B of the invention. The urine collection vessel 10B is shown in greater detail in FIGS. 4 and 5. The vessel 10B has a urine collection void 22 as determined by curved wall 23. Wall 23 defines an elongate vessel having a curvature complementary to that of the female anatomy in the pubic region. When looking into the void 22, as in the illustration of FIG. 4, one sees a flat peripheral area 21 surrounding and framing void 22. This flat, peripheral area 21 rests against the body skin of the female 12B and is coupled to her body by a partial vacuum created within the vessel 10B in a manner similar to that of the partial vacuum created in sheath 11 of the male of FIG. 1.

When conduit 13 is connected to the female urine collection vessel 10B and connected to reservoir 14, the system functions in the same manner as that described with respect to the male sheath 11 in FIG. 1. Adjustment of air flow control valve 16 adjusts the degree with which a partial vacuum is achieved within vessel 10B and therefore the degree of adherence of the vessel to the female anatomy. As before, adjustment of valve 16 also controls the velocity of air flow A through conduit 13. The ability to control the velocity may be utilized to enhance the flow of air and urine through conduit 13.

Because of the differences between male and female anatomy, it may be necessary that the female shave some of the pubic hair which may lie in the region in which the flat peripheral area 21 of vessel 10B will come into contact. It may also be desirable for the female user of collection vessel 10B to spread a salve or a petroleum jelly like substance on the surface of flat peripheral area 21 to further assure a vacuum induced adhesion of vessel 10B to the body of female 12B.

Most women patients seem to appreciate the added assurance they receive by wearing a pair of elasticized panties which have been modified to provide an outlet opening for conduit 11 as well as access to air flow control valve 16. This is primarily a psychological reassurance and women who do not move about violently in the course of the night's sleep will have little to concern them for fear of dislodging the collection vessel 10B.

What has been described is a urine collection vessel which is coupled to the body of a person by means of a partial vacuum created within the collection vessel. An air flow valve at the output of the vessel is adjustable to control the degree of a partial vacuum created within the vessel as well as establishing control over the velocity of air flow through the valve and down the associated conduit through which urine is conducted to a reservoir in which the urine is accumulated. The device is intended for use primarily by people who are troubled with prostate or bladder problems which, without the use of the invention, would make it necessary for these persons to frequently fully rouse themselves from sleep and to exit from their beds in order to void their bladders in the course of the night.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such clear and concise manner that those skilled in the art may readily understand and practice the invention, That which is claimed:

1. In apparatus for the receiving, transferring, and accumulating of fluids excreted from the body and having fluid collection means to be coupled to the body for receiving said fluids, reservoir means for accumulating said fluids, hollow conduit means for transferring said fluids from said collection means to said reservoir means, and air flow impelling means for drawing air into said collector means, through said conduit means and said reservoir, to enhance the flow of said fluid from said collector means to said reservoir means, the improvement comprising:
 adjustable air flow control means coupled to said collection means for selectively reducing air flow through said conduit and for:
 a. creating a partial vacuum within said collection means whereby said collection means is retained in place on the body, and
 b. for increasing the velocity of air flowing through said conduit whereby the flow of excreted body fluids from said collection means to said reservoir means through said conduit means is aided and enhanced.

2. The improvement of claim 1 further comprising variable control means for varying the degree of reduction of air flow through said conduit
 a. for adjusting the degree of said partial vacuum within said collection means as dictated by the comfort of the person on whose body said collection means is retained by said partial vacuum, and
 b. for adjusting the air flow rate of evacuation of fluid from said collection means.

3. The improvement of claim 2 wherein said air flow means is a continuously operating air pump.

4. The improvement of claim 3 wherein said air flow means is a vibratory air pump.

5. The improvement of claim 4 wherein said vibratory air pump is of the type which outputs a soothing sound tending to relax a person and induce sleep.

6. The improvement of claim 2 wherein said collection means is a condom-like sheath which accepts the male penis and is retained on said penis by the partial vacuum created by said air flow control means.

7. The improvement of claim 6 wherein said air flow means is a continuously operating air pump.

8. The improvement of claim 7 wherein said air flow means is a vibratory air pump.

9. The improvement of claim 8 wherein said vibratory air pump is of the type which outputs a soothing sound tending to relax a person and induce sleep.

10. The improvement of claim 2 wherein said collection means is a fluid collection vessel conforming to the anatomy of a women's pubic region which encompasses the female urinary outlet area and is retained coupled to the female body by the partial vacuum created by said air flow control means.

11. The improvement of claim 10 wherein said air flow means is a continually operating air pump.

12. The improvement of claim 11 wherein said air flow means is a vibratory air pump.

13. The improvement of claim 12 wherein said vibratory air pump is of the type which outputs a soothing sound tending to relax a person and induce sleep.

* * * * *